United States Patent [19]
Rhyne et al.

[11] Patent Number: 5,961,463
[45] Date of Patent: Oct. 5, 1999

[54] NONLINEAR IMAGING USING ORTHOGONAL TRANSMIT AND RECEIVE CODES

[75] Inventors: Theodore L. Rhyne, Whitefish Bay, Wis.; Richard Y. Chiao, Clifton Park, N.Y.

[73] Assignee: General Electric Company, Milwaukee, Wis.

[21] Appl. No.: 09/138,636

[22] Filed: Aug. 24, 1998

[51] Int. Cl.$^6$ ........................................................ A61B 8/14
[52] U.S. Cl. .............................................................. 600/458
[58] Field of Search ................................... 600/443, 444, 600/447, 458; 424/9.52; 367/7

[56] References Cited

U.S. PATENT DOCUMENTS

| | | | |
|---|---|---|---|
| 5,632,277 | 5/1997 | Chapman et al. | 128/660.07 |
| 5,706,819 | 1/1998 | Hwang et al. | 128/662.02 |
| 5,860,931 | 1/1999 | Chandler | 600/458 |
| 5,882,306 | 3/1999 | Ramamurthy et al. | 600/440 |
| 5,897,500 | 4/1999 | Zhao | 600/443 |

OTHER PUBLICATIONS

Frank, "Polyphase Complementary Codes", IEEE Trans. Inform. Theory, vol. IT–26, No. 6, Nov. 1980, pp. 641–647.
Sivaswamy, "Multiphase Complementary Codes", IEEE Trans. Inform. Theory, vol. IT–24, No. 5, Sep. 1978, pp. 546–552.
Tseng, "Complementary Sets of Sequences," IEEE Trans. Inform. Theory, vol. IT–18, No. 5, Sep. 1972, pp. 644–652.
Golay, "Complementary Series," IRE Trans. Inform. Theory, Apr. 1961, pp. 82–87.
Lee et al., "High–Speed Digital Golay Code Flaw Detection System," Proc. 1981 Ultrasonics Symp., pp. 888–891.
Hayward et al., "A Digital Hardware Correlation System for Fast Ultrasonic Data Acquisition in Peak Power Limited Applications," IEEE Trans. Ultrason. Ferroelec. Freq. Cont., vol. 35, No. 6, Nov. 1988, pp. 800–808.
Mayer et al., "Three–Dimensional Imaging System Based on Fourier Transform Synthetic Aperture Focusing Technique," Ultrasonics, vol. 28, Jul. 1990, pp. 241–255.
Takeuchi, "An Investigation of a Spread Energy Method for Medical Ultrasound Systems. II. Proposed System and Possible Problems," Ultrasonic, vol. 17, Sep. 1979, pp. 219–224.
O'Donnell, "Coded Excitation System for Improving the Penetration of Real–Time Phased–Array Imaging Systems," IEEE Trans. Ultrason. Ferroelec. Freq. Cont., vol. 39, No. 3, May 1992, pp. 341–351.

*Primary Examiner*—Francis J. Jaworski
*Assistant Examiner*—Ali M. Imam
*Attorney, Agent, or Firm*—Dennis M. Flaherty; Christian G. Cabou; Phyllis Y. Price

[57] ABSTRACT

A method and an apparatus for imaging the nonlinear components of an ultrasound signal returned from ultrasound scatterers in tissue or contrast agents in blood. The method employs a code-modulated wavelet for transmission combined with correlation filtering on reception. Transmit codes are used to modulate the phases of wavelets for successive transmit firings focused at the same transmit focal position. For example, for a first transmit firing a first transmit code is used to modulate a base wavelet to form a first coded wavelet and for a second transmit firing a second transmit code is used to modulate the same base wavelet to form a second coded wavelet. On reception, the receive signals resulting from the first and second transmit firings are decoded by correlating the receive signals with first and second receive codes respectively. The transmit and receive codes satisfy the orthogonality condition that the sum of the correlation of the first transmit code with the first receive code and the correlation of the second transmit code with the second receive code equals zero. The combined transmission and reception operations will exactly cancel the linear echo component of the signal, leaving the nonlinear components for imaging.

14 Claims, 3 Drawing Sheets

NONLINEAR IMAGING USING ORTHOGONAL TRANSMIT AND RECEIVE CODES

FIELD OF THE INVENTION

This invention generally relates to ultrasound imaging of the human anatomy for the purpose of medical diagnosis. In particular, the invention relates to methods and apparatus for imaging ultrasound echo components arising from nonlinear propagation and scattering in tissue or contrast agents in blood.

BACKGROUND OF THE INVENTION

Conventional ultrasound scanners create two-dimensional B-mode images of tissue in which the brightness of a pixel is based on the intensity of the echo return. Alternatively, in a color flow imaging mode, the movement of fluid (e.g., blood) or tissue can be imaged. Measurement of blood flow in the heart and vessels using the Doppler effect is well known. The frequency shift of backscattered ultrasound waves may be used to measure the velocity of the backscatterers from tissue or blood. The Doppler shift may be displayed using different colors to represent speed and direction of flow. In power Doppler imaging, the power contained in the returned Doppler signal is displayed.

Conventional ultrasound transducers transmit a broadband signal centered at a fundamental frequency $f_0$, which is applied separately to each transducer element making up the transmit aperture by a respective pulser. The pulsers are activated with time delays that produce the desired focusing of the transmit beam at a particular transmit focal position. As the transmit beam propagates through tissue, echoes are created when the ultrasound wave is scattered or reflected off of the boundaries between regions of different density. The transducer array is used to transduce these ultrasound echoes into electrical signals, which are processed to produce an image of the tissue. These ultrasound images are formed from a combination of fundamental and harmonic signal components, the latter of which are generated in a nonlinear medium such as tissue or a blood stream containing contrast agents. With linear scattering, the received signal is a time-shifted, amplitude-scaled version of the transmitted signal. This is not true for acoustic media which scatter ultrasound in a nonlinear manner.

The echoes from a high-level signal transmission will contain both linear and nonlinear signal components. In the theory of nonlinear circuits, the signals are expressed as an infinite sum of signal components. The first term in this sum is the linear term and the higher-order terms represent signals whose spectra are multiple convolutions (in frequency) of the original spectrum. This means that much more spectral energy than only the second harmonic is created.

In certain instances ultrasound images may be improved by suppressing the fundamental and emphasizing the harmonic (nonlinear) signal components. If the transmitted center frequency is at $f_0$, then tissue/contrast nonlinearities will generate harmonics at $kf_0$, where k is an integer greater than or equal to 2. Imaging of harmonic signals has been performed by transmitting a narrowband signal at frequency $f_0$ and receiving at a band centered at frequency $2f_0$ (second harmonic) followed by receive signal processing.

A nonlinear imaging system using phase inversion subtraction is disclosed in U.S. Pat. No. 5,632,277 to Chapman et al. First and second ultrasound pulses are transmitted into the specimen being imaged in sequence and the resulting receive signals are summed. The first and second pulses differ in phase by 180°. If the ultrasound waves undergo nonlinear propagation or nonlinear interaction with contrast agents or other nonlinear scattering media, then the returned signal will have both linear and nonlinear components. Upon summation, the linear components will cancel, leaving only the nonlinear components to be imaged.

There is a need for an alternative method of isolating the nonlinear components of the echo signals for use in both non-contrast and contrast harmonic imaging.

SUMMARY OF THE INVENTION

The present invention is a method and an apparatus for imaging the nonlinear components of an ultrasound signal returned from ultrasound scatterers in tissue or contrast agents in blood. The method employs a code-modulated wavelet for transmission combined with correlation filtering on reception. As used herein, the term "wavelet" includes arbitrary analog signals not having discrete times and amplitudes as well as pulse sequences having discrete times and amplitudes. The combined transmission and reception operations will substantially cancel the linear echo component of the signal, leaving the nonlinear components for imaging.

In accordance with a preferred embodiment of the invention, transmit codes are used to modulate the phases of wavelets for successive transmit firings focused at the same transmit focal position. For example, for a first transmit firing a first transmit code is used to modulate a base wavelet to form a first coded wavelet and for a second transmit firing a second transmit code is used to modulate the same base wavelet to form a second coded wavelet. On reception, the receive signals resulting from the first and second transmit firings are decoded by correlating the receive signals with first and second receive codes respectively. The transmit and receive codes satisfy an orthogonality condition, to wit, that the sum of the correlation of the first transmit code with the first receive code and the correlation of the second transmit code with the second receive code equals zero.

As a result of using transmit and receive codes satisfying the orthogonality condition, the correlation of the first receive signal (produced by the first transmit firing) with the first receive code produces a first filtered receive signal, while the correlation of the second receive signal (produced by the second transmit firing) with the second receive code produces a second filtered receive signal. The first and second filtered receive signals are opposite in phase for the fundamental (i.e., linear) signal such that the summation of the two filtered receive signals substantially cancels the linear echo signal, leaving the nonlinear signal components for signal processing and imaging.

In accordance with the preferred embodiment of the invention, the correlation filtering is performed on the beam-summed signal before demodulation. However, correlation filtering could alternatively be performed on the beam-summed and demodulated signal. If the demodulator precedes the correlation filter, then the orthogonality condition must be satisfied for the receive codes and the demodulated transmit codes.

DETAILED DESCRIPTION OF THE PREFERRED EMBODIMENTS

Figure 1:
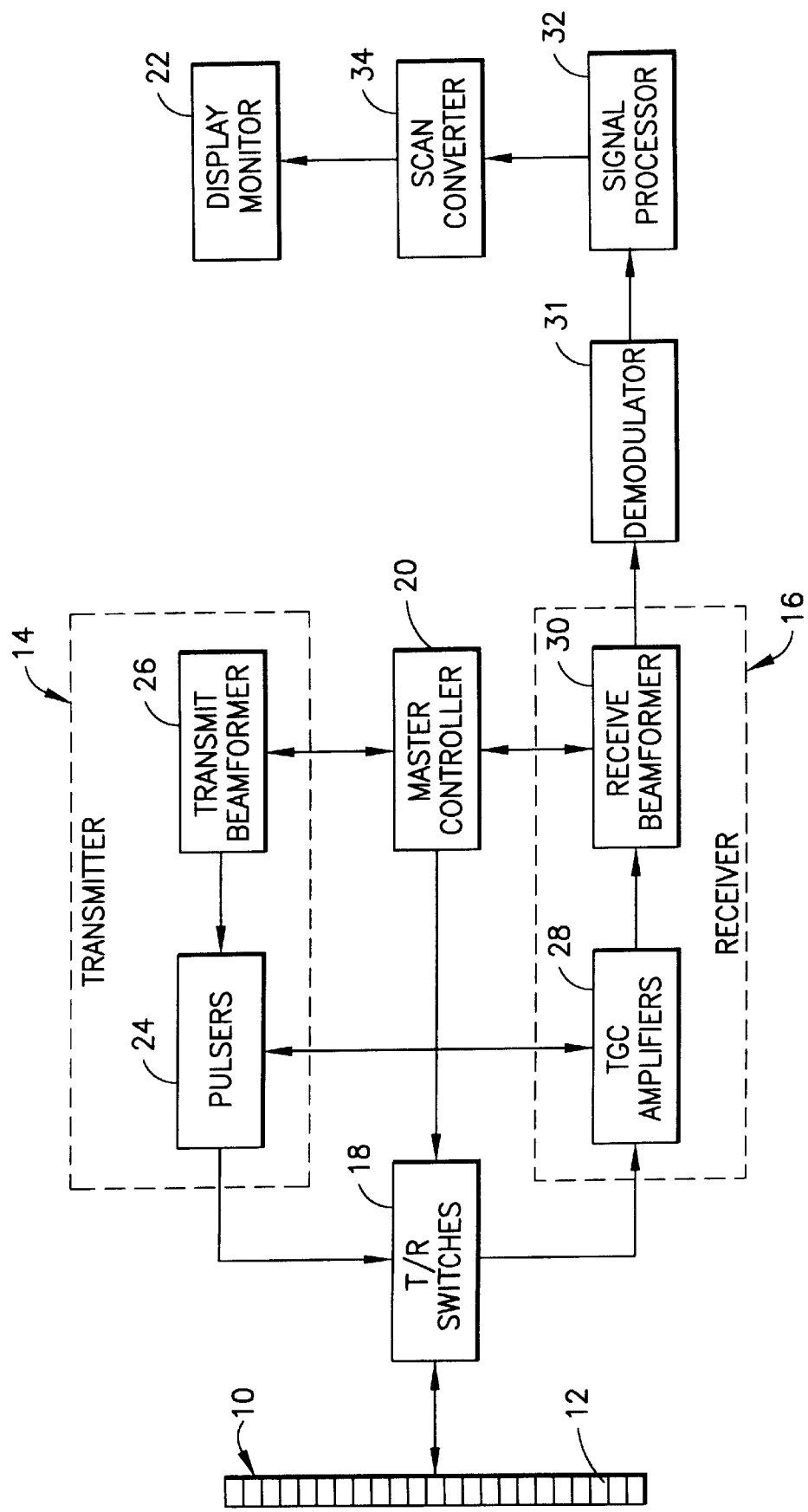
FIG. 1 is a block diagram showing an ultrasound imaging system which can be programmed to incorporate the present invention.

An ultrasonic imaging system which incorporates the present invention is depicted in FIG. 1. The system comprises a transducer array 10 consisting of a plurality of separately driven transducer elements 12, each of which produces a burst of ultrasonic energy when energized by a pulsed waveform produced by a transmitter 14. The ultrasonic energy reflected back to transducer array 10 from the object under study is converted to an electrical signal by each receiving transducer element 12 and applied separately to a receiver 16 through a set of transmit/receive (T/R) switches 18. The T/R switches 18 are typically diodes which protect the receive electronics from the high voltages generated by the transmit electronics. The transmit signal causes the diodes to shut off or limit the signal to the receiver. Transmitter 14 and receiver 16 are operated under control of a master controller 20 responsive to commands by a human operator. A complete scan is performed by acquiring a series of echoes in which transmitter 14 is gated ON momentarily to energize each transducer element 12, and the subsequent echo signals produced by each transducer element 12 are applied to receiver 16. A channel may begin reception while another channel is still transmitting. The receiver 16 combines the separate echo signals from each transducer element to produce a single echo signal which is used to produce a line in an image on a display monitor 22.

Under the direction of master controller 20, the transmitter 14 drives transducer array 10 such that the ultrasonic energy is transmitted as a directed focused beam. To accomplish this, respective time delays are imparted to a multiplicity of pulsers 24 by a transmit beamformer 26. The master controller 20 determines the conditions under which the acoustic pulses will be transmitted. With this information, the transmit beamformer 26 will determine the timing and the amplitudes of each of the transmit pulses to be generated by pulsers 24. The amplitudes of each transmit pulse are generated by an apodization generation circuit (not shown). The pulsers 24 in turn send the transmit pulses to each of the elements 12 of the transducer array 10 via the T/R switches 18, which protect the time-gain control (TGC) amplifiers 28 from the high voltages which may exist at the transducer array. By appropriately adjusting the transmit focus time delays and the apodization weightings in a conventional manner, an ultrasonic beam can be directed and focused to form a transmit beam.

The echo signals produced by each burst of ultrasonic energy reflect from objects located at successive ranges along each transmit beam. The echo signals are sensed separately by each transducer element 12 and a sample of the magnitude of the echo signal at a particular point in time represents the amount of reflection occurring at a specific range. Due to the differences in the propagation paths between a reflecting point and each transducer element 12, the echo signals will not be detected simultaneously and their amplitudes will not be equal. Receiver 16 amplifies the separate echo signals via a respective TGC amplifier 28 in each receive channel. The amount of amplification provided by the TGC amplifiers is controlled through a control line (not shown). The amplified echo signals are then fed to the receive beamformer 30. Each receiver channel of the receive beamformer is connected to a respective one of the transducer elements 12 by a respective TGC amplifier 28.

Under the direction of master controller 20, the receive beamformer 30 tracks the direction of the transmitted beam, sampling the echo signals at a succession of ranges along each beam. The receive beamformer 30 imparts the proper time delays and receive apodization weightings to each amplified echo signal and sums them to provide an echo signal which accurately indicates the total ultrasonic energy reflected from a point located at a particular range along one ultrasonic beam. The receive focus time delays are computed in real-time using specialized hardware or are read from a look-up table. The receive channels also have circuitry for filtering the received pulses. The time-delayed receive signals are then summed.

In the conventional system, the frequency of the beamformer output is shifted to baseband by a demodulator 31. One way of achieving this is to multiply the input signal by a complex sinusoidal $e^{i2\pi f_d t}$, where $f_d$ is the frequency shift required to bring the signal spectrum to baseband. The beamsummed and demodulated signal is then output to a signal processor 32. The signal processor 32 converts the summed receive signals to display data. In the B-mode (gray-scale), this would be the envelope of the signal with some additional processing, such as edge enhancement and logarithmic compression. The scan converter 34 receives the display data from signal processor 32 and converts the data into the desired image for display. In particular, the scan converter 34 converts the acoustic image data from polar coordinate (R-θ) sector format or Cartesian coordinate linear array to appropriately scaled Cartesian coordinate display pixel data at the video rate. This scan-converted acoustic data is then output for display on display monitor 22, which images the time-varying amplitude of the envelope of the B-mode signal as a gray scale. A respective scan line is displayed for each transmit beam.

Figure 2:
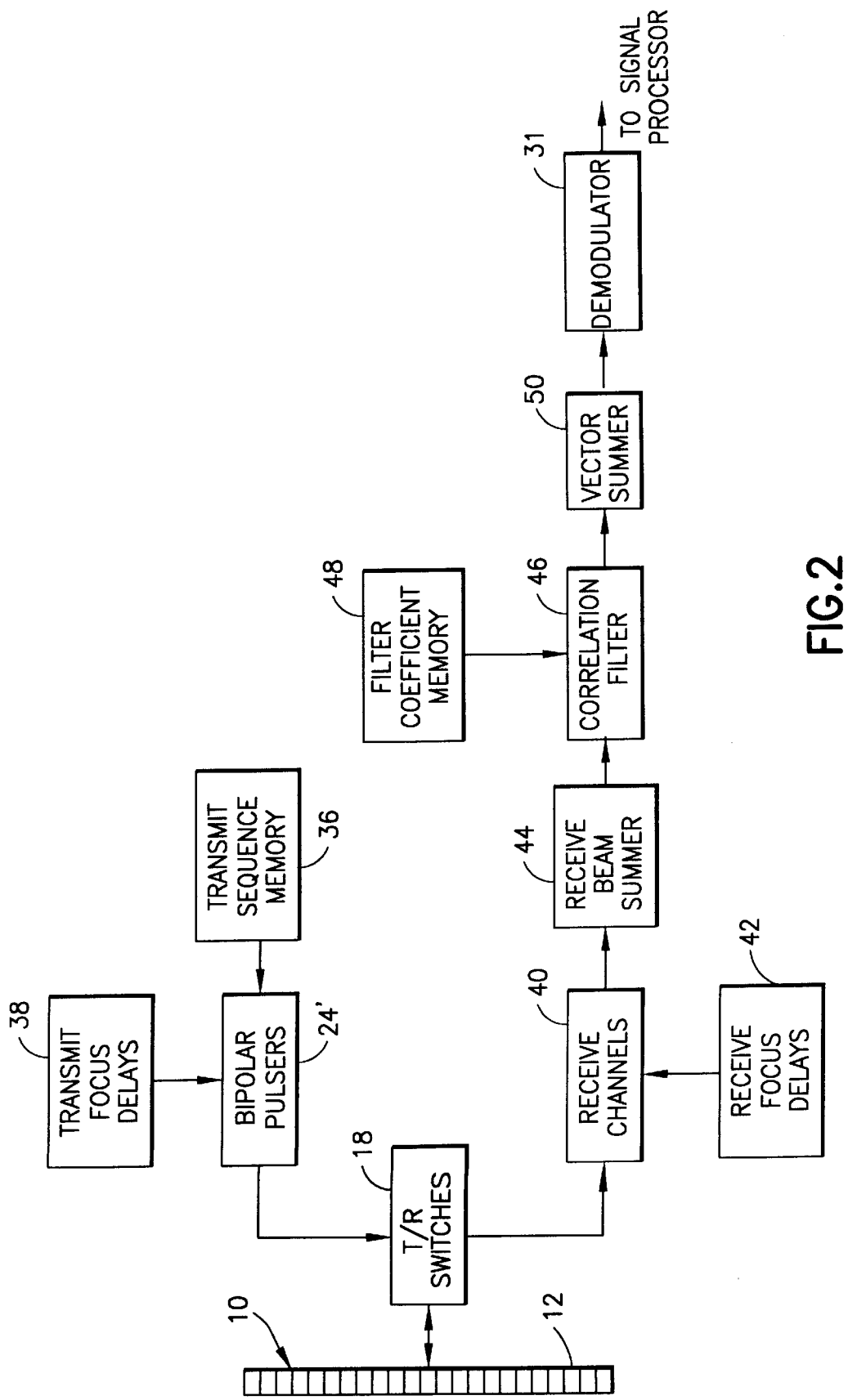
FIG. 2 is a block diagram showing an ultrasound imaging system in accordance with the invention.

FIG. 2 shows an ultrasound flow imaging system in accordance with the present invention. In this system each transducer element in the transmit aperture is pulsed using a coded sequence of a base wavelet, each pulse in the sequence being commonly referred to as a chip. The base wavelet is phase encoded, using N-digit transmit codes, to create N-chip coded wavelets which are stored in transmit sequence memory 38. Each coded wavelet read out of transmit sequence memory 38 controls activation of a multiplicity of bipolar pulsers 24' during a respective transmit firing. For example, the transducer elements are pulsed in accordance with a first coded wavelet during a first transmit firing focused at a desired transmit focal position and in accordance with a second coded wavelet during a second transmit firing focused at the same transmit focal position. The first and second coded wavelets are generated by respectively convolving first and second transmit codes with the base wavelet, i.e., by phase encoding the base wavelet using the transmit codes. In accordance with a preferred embodiment of the invention, the first and second transmit codes are complementary Golay codes, e.g., the Golay code pair [1,1] and [1,−1].

The bipolar pulsers 24' drive the elements 12 of transducer array 10 such that the ultrasonic energy produced is focused in a beam for each transmit firing. To accomplish this, transmit focus time delays 38 are imparted to the respective pulsed waveforms output by the pulsers. By appropriately adjusting the transmit focus time delays in a conventional manner, the ultrasonic beams can be focused at a multiplicity of transmit focal positions to effect a scan in an image plane.

For each transmit, the echo signals from the transducer elements 12 are fed to respective receive channels 40 of the receive beamformer. Each receive channel has an analog-to-digital converter. Under the direction of the master controller (item 20 in FIG. 1), the receive beamformer tracks the direction of the transmitted beam. The receive beamformer memory 42 imparts the proper receive focus time delays to the received echo signal and sums them to provide an echo signal which accurately indicates the total ultrasonic energy reflected from a particular transmit focal position. The time-delayed receive signals are summed in receive summer 44 for each transmit firing.

The summed receive signals from successive firings are output to a correlation filter 46, which correlates the first summed receive signal with the first receive code for the first transmit firing and the second summed receive signal with the second receive code for the second transmit firing. In accordance with the preferred embodiment of the invention, the first and second receive codes form a complementary Golay code pair and are orthogonal to the first and second transmit codes.

The filtered signals derived from the first and second transmit firings focused at the same transmit focal position are summed in vector summer 50 and the summed filtered signals are then demodulated and output to the signal processor.

In the B mode, signal processing includes envelope detection, edge enhancement and logarithmic compression. Following signal processing and scan conversion, a scan line is displayed on the display monitor (22 in FIG. 1). This procedure is repeated so that a respective scan line is displayed for each transmit focal position (in the case of one transmit focal position for each beam angle) or for each vector (in the case of multiple transmit focal positions for each beam angle).

Although a preferred embodiment using complementary Golay code pairs has been disclosed, the invention encompasses the use of any transmit and receive codes which satisfy the orthogonality condition that the sum of the correlation of the first transmit code with the first receive code and the correlation of the second transmit code with the second receive code equals zero. In mathematical terms, if the first transmit code and first receive code are designated X1 and X2 respectively, and the second transmit code and second receive code are designated X3 and X4 respectively, then X1, X2, X3 and X4 must satisfy the following orthogonality condition:

$$(X1 \otimes X2) + (X3 \otimes X4) = 0$$

where $\otimes$ denotes correlation.

Figure 3:
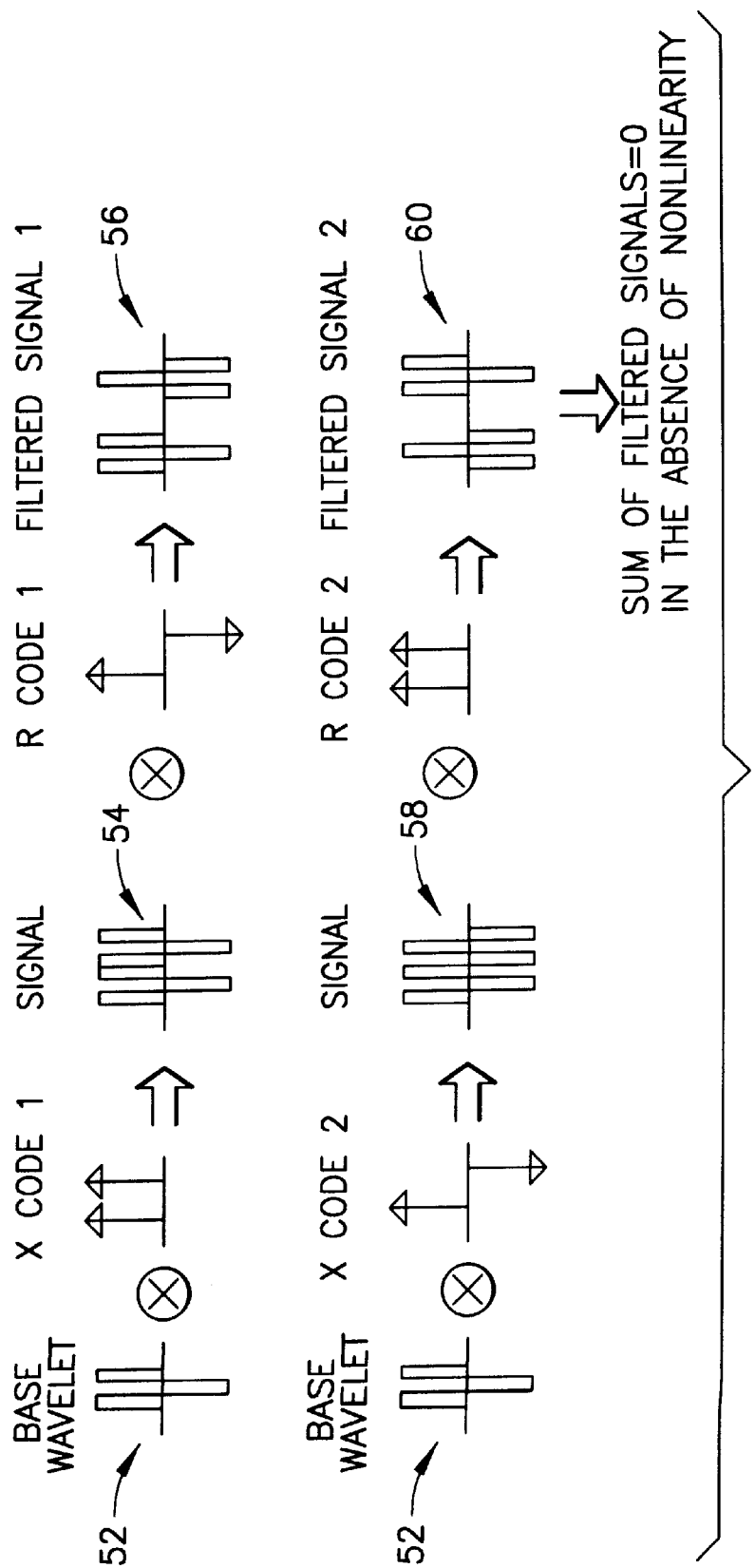
FIG. 3 is a schematic showing the use of orthogonal Golay code pairs to modulate a transmit pulse waveform and then process the resulting receive signals in accordance with a preferred embodiment of the invention.

FIG. 3 shows the effect of the preferred embodiment on linearly reflected signals. For the first firing, a base wavelet 52 is convolved by a first transmit code (X Code 1) [1,1] to generate a first transmit signal 54. When a perfect copy of the first transmit signal 54 is correlated with a first receive code (R Code 1) [1,−1] in the correlation filter, the filtered signal 56 is produced. For the second firing, a second transmit signal 58 is generated by convolving a second transmit code (X Code 2) [1,−1] with the base wavelet 52. When a perfect copy of the second transmit signal 58 is correlated with a second receive code (R Code 2) [1,1] in the correlation filter, the filtered signal 60 is produced. When the filtered signals 56 and 60 are summed, a pulse of magnitude zero results, i.e., the linear components will cancel. However, the nonlinear signal components do not have the same coherence as the linear signal components and will not be canceled. Therefore the resulting image will show these nonlinear components.

The coding scheme shown in FIG. 3 is one example of using an orthogonal Golay code for nonlinear imaging. Other orthogonal codes exist and can be used for the same purpose. For good range resolution, it is desirable to use short codes as in the preferred embodiment, so the shorter codes are of the greatest value. There may be certain advantages in the selection of the particular code and the particular pulse signal, in that the particular codes and signals may enhance the nonlinear phenomena that is desired.

In accordance with the preferred embodiment of the invention, the correlation filter 46 comprises an FIR filter having N filter taps for receiving a set of N filter coefficients from a filter coefficient memory 48, where N is the number of digits of the orthogonal code. For each transmit firing, the filter coefficients $c_0, c_1, \ldots, C_{N-1}$ have scalar values equal to the respective digits of the respective receive code. The filter coefficients, like the transmit and receive time delays and the transmit codes, can be supplied by the master controller. Filter 46 outputs the filtered signals to vector summer 50, which sums them to substantially cancel the linear component.

The foregoing preferred embodiments have been disclosed for the purpose of illustration. Variations and modifications which fall within the broad concept of the invention will be readily apparent to those skilled in the art. All such variations and modifications are intended to be encompassed by the claims set forth hereinafter.

We claim:

1. A system for nonlinear imaging of ultrasound scatterers, comprising:

an ultrasound transducer array comprising a multiplicity of transducer elements;

a transmitter coupled to said transducer array for pulsing a set of selected transducer elements which form a transmit aperture with a first coded wavelet during a first transmit firing and with a second coded wavelet during a second transmit firing, said first coded wavelet being derived by coding a base wavelet with a first transmit code and said second coded wavelet being derived by coding said base wavelet with a second transmit code;

acquisition means coupled to said transducer array for acquiring first and second beamsummed receive signals subsequent to said first and second transmit firings respectively;

a filter for correlating said first beamsummed receive signal with a first receive code to form a first filtered signal and correlating said second beamsummed receive signal with a second receive code to form a second filtered signal;

means for vector summing said first and second filtered signals to produce a summed signal;

a processor programmed to form an image signal from said summed signal; and means for displaying an image which is a function of said image signal, wherein the correlation of said first transmit code with said first receive code summed with the correlation of said second transmit code with said second receive code equals zero.

2. The system as defined in claim 1, wherein said filter is programmed with a first set of filter coefficients for correlating said first beamsummed receive signal and with a second set of filter coefficients for correlating said second beamsummed receive signal, said first set of filter coefficients matching said first receive code and said second set of filter coefficients matching said second receive code.

3. The system as defined in claim 1, wherein said first and second transmit codes form a first complementary Golay code pair, and said first and second receive codes form a second complementary Golay code pair.

4. The system as defined in claim 1, wherein said first transmit code and said second receive code are both [1,1], and said second transmit code and said first receive code are both [1,−1].

5. A method for imaging ultrasound scatterers, comprising the steps of:
producing a first coded wavelet which is a function of a first transmit code convolved with a base wavelet and a second coded wavelet which is a function of a second transmit code convolved with said base wavelet;
driving transducer elements with said first coded wavelet during a first transmit firing and with said second coded wavelet during a second transmit firing, said first and second transmit firings being focused at a transmit focal position;
receiving first and second sets of echo signals from transducer elements subsequent to said first and second transmit firings respectively;
forming first and second beamsummed receive signals derived from said first and second sets of echo signals respectively;
correlating said first beamsummed receive signal with a first receive code to form a first filtered signal;
correlating said second beamsummed receive signal with a second receive code to form a second filtered signal;
vector summing said first and second filtered signals to produce a summed signal;
processing said summed signal to form an image signal; and
displaying an image which is a function of said image signal,
wherein the correlation of said first transmit code with said first receive code summed with the correlation of said second transmit code with said second receive code equals zero.

6. The method as defined in claim 5, wherein said first and second transmit codes form a first complementary Golay code pair, and said first and second receive codes form a second complementary Golay code pair.

7. The method as defined in claim 5, wherein said first transmit code and said second receive code are both [1,1], and said second transmit code and said first receive code are both [1,−1].

8. The method as defined in claim 5, wherein said first set of transducer elements is focused at the same focal position during said first and second transmit firings.

9. A system for nonlinear imaging of ultrasound scatterers, comprising:
an ultrasound transducer array comprising a multiplicity of transducer elements;
a transmitter coupled to said transducer array for pulsing said transducer elements with a first coded wavelet during a first transmit firing and with a second coded wavelet during a second transmit firing, said first coded wavelet being derived by coding a base wavelet with a first transmit code and said second coded wavelet being derived by coding said base wavelet with a second transmit code;
a receiver coupled to said transducer array for receiving a first set of signals from said transducer following said first transmit firing and a second set of signals from said transducer elements following said second transmit firing;
a beamformer for forming first and second beamsummed receive signals from said first and second sets of signals respectively;
a filter arranged to correlate said first beamsummed receive signal with a first receive code to form a first filtered signal and correlates said second beamsummed receive signal with a second receive code to form a second filtered signal;
a vector summer for summing said first and second filtered signals to produce a summed signal;
a processor programmed to form an image signal from said summed signal; and
means for displaying an image which is a function of said image signal,
wherein the correlation of said first transmit code with said first receive code summed with the correlation of said second transmit code with said second receive code equals zero.

10. The system as defined in claim 9, wherein said filter is programmed with a first set of filter coefficients for correlating said first beamsummed receive signal and with a second set of filter coefficients for correlating said second beamsummed receive signal, said first set of filter coefficients matching said first receive code and said second set of filter coefficients matching said second receive code.

11. The system as defined in claim 9, wherein said first and second transmit codes form a first complementary Golay code pair, and said first and second receive codes form a second complementary Golay code pair.

12. The system as defined in claim 9, wherein said first transmit code and said second receive code are both [1,1], and said second transmit code and said first receive code are both [1,−1].

13. A system for nonlinear imaging of ultrasound scatterers, comprising:
an ultrasound transducer array comprising a multiplicity of transducer elements;
transmit means coupled to said transducer array for pulsing a set of selected transducer elements which form a transmit aperture with a first coded wavelet during a first transmit firing and with a second coded wavelet during a second transmit firing, said first coded wavelet being derived by coding a base wavelet with a first transmit code and said second coded wavelet being derived by coding said base wavelet with a second transmit code;
acquisition means coupled to said transducer array for acquiring first and second beamsummed receive signals subsequent to said first and second transmit firings respectively;
demodulation means for demodulating said first and second beamsummed receive signals to form first and second demodulated signals respectively;
a filter for correlating said first demodulated signal with a first receive code to form a first filtered signal and correlating said second demodulated signal with a second receive code to form a second filtered signal;
means for vector summing said first and second filtered signals to produce a summed signal;
a processor programmed to form an image signal from said summed signal; and
means for displaying an image which is a function of said image signal, wherein the correlation of a demodulated version of said first transmit code with said first receive code summed with the correlation of a demodulated version of said second transmit code with said second receive code equals zero.

14. A method for imaging ultrasound scatterers, comprising the steps of:

producing a first coded wavelet which is a function of a first transmit code convolved with a base wavelet and a second coded wavelet which is a function of a second transmit code convolved with said base wavelet;

driving transducer elements with said first coded wavelet during a first transmit firing and with said second coded wavelet during a second transmit firing, said first and second transmit firings being focused at a transmit focal position;

receiving first and second sets of echo signals from transducer elements subsequent to said first and second transmit firings respectively;

forming first and second beamsummed receive signals derived from said first and second sets of echo signals respectively;

demodulating said first and second beamsummed receive signals to form first and second demodulated signals respectively;

correlating said first demodulated signal with a first receive code to form a first filtered signal;

correlating said second demodulated signal with a second receive code to form a second filtered signal;

vector summing said first and second filtered signals to produce a summed signal;

processing said summed signal to form an image signal; and displaying an image which is a function of said image signal, wherein the correlation of a demodulated version of said first transmit code with said first receive code summed with the correlation of a demodulated version of said second transmit code with said second receive code equals zero.

* * * * *